(12) United States Patent
Auvin et al.

(10) Patent No.: US 10,195,221 B2
(45) Date of Patent: Feb. 5, 2019

(54) EFFERVESCENT FORMULATION BASED ON PYRIDOXAL-5-PHOSPHATE

(71) Applicant: Assistance Publique-Hopitaux De Paris, Paris (FR)

(72) Inventors: Stéphane Auvin, Vendeville (FR); Thomas Storme, L'ile St-Denis (FR); Pascal Vaconsin, L'ile St-Denis (FR); Vincent Boudy, Paris (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 0 days.

(21) Appl. No.: 15/740,491

(22) PCT Filed: Jun. 29, 2016

(86) PCT No.: PCT/IB2016/053885
§ 371 (c)(1),
(2) Date: Dec. 28, 2017

(87) PCT Pub. No.: WO2017/002034
PCT Pub. Date: Jan. 5, 2017

(65) Prior Publication Data
US 2018/0303854 A1 Oct. 25, 2018

(30) Foreign Application Priority Data
Jun. 30, 2015 (FR) .................................... 15 56142

(51) Int. Cl.
| | |
|---|---|
| A61K 31/675 | (2006.01) |
| A61K 9/48 | (2006.01) |
| A61P 25/08 | (2006.01) |
| A61K 9/46 | (2006.01) |
| A61P 3/02 | (2006.01) |
| A61K 47/26 | (2006.01) |
| A61K 47/02 | (2006.01) |
| A61K 33/00 | (2006.01) |

(52) U.S. Cl.
CPC .......... *A61K 31/675* (2013.01); *A61K 9/0007* (2013.01); *A61K 9/4858* (2013.01); *A61K 47/02* (2013.01); *A61K 47/26* (2013.01); *A61P 3/02* (2018.01); *A61P 25/08* (2018.01); *A61K 33/00* (2013.01); *A61K 2300/00* (2013.01)

(58) Field of Classification Search
CPC combination set(s) only.
See application file for complete search history.

(56) References Cited

FOREIGN PATENT DOCUMENTS

| | | |
|---|---|---|
| CA | 1340246 | 12/1998 |
| WO | WO 2014/159659 | 10/2014 |

OTHER PUBLICATIONS

Search Report and Written Opinion from PCT Application No. PCT/IB2016/053885, dated Sep. 16, 2016.
Serrano et al., "TCH-011 Development of Pyridoxal-5-Phosphate Hard Capsules for Paediatric Use," European Journal of Hospital Pharmacy, vol. 20, No. Supp_1, Mar. 1, 2013, pp. A72-A72.
Wang, "Pyridoxal phosphate is better than pyridoxine for controlling idiopathic intractable epilepsy," Archives of Disease in Childhood, vol. 90, No. 5, May 1, 2005, pp. 512-515.

*Primary Examiner* — Trevor Love
(74) *Attorney, Agent, or Firm* — Alston & Bird LLP

(57) ABSTRACT

Provided is a fast-dissolving effervescent pharmaceutical formulation of pyridoxal-5-phosphate, and to the use thereof in the treatment of neonatal epilepsy and also of metabolic disorders with a need for pyridoxal-5-phosphate.

5 Claims, 4 Drawing Sheets

EFFERVESCENT FORMULATION BASED ON PYRIDOXAL-5-PHOSPHATE

FIELD

The invention relates to an effervescent formulation comprising pyridoxal-5-phosphate, the method of preparation thereof and the use thereof in the treatment of neonatal epilepsy.

BACKGROUND

Pyridoxal-5-phosphate (P5P) should be administered to all neonates who have epileptic seizures and have not responded to first-line treatment.

The incidence of seizures is higher in the neonatal period than at any other time of life (0.7 to 2.7 per 1000 live births) [1, 2]. The first-line treatment is phenobarbital. Response to the treatment is 50% [3]. In nonresponders, the possibility of vitamin-sensitive epilepsy should be considered. There are two main entities: pyridoxonidependent epilepsy (OMIM 266100) and pyridoxamine 5-phosphate oxidase deficiency (OMIM 610090). In these two diseases, early administration of pyridoxal phosphate may control the epileptic seizures. The recommendations are therefore to treat all neonates and young babies who have epileptic seizures not responding to the first-line treatments. If the diagnosis is confirmed, the treatment is administered for life.

Pyridoxal-5-phosphate or pyridoxal phosphate, also designated P5P or P5P-H hereinafter, is a vitamin that is indispensable in the management of neonatal epileptic seizures and will be maintained for life in patients for whom the diagnosis of vitamin-sensitive epilepsy is confirmed. To date, there is no pharmaceutical specialty intended for humans in a form that is suitable for pediatrics. P5P is currently supplied to some neonatal medicine departments in the form of preparations produced according to customary local conditions, generally containing microcrystalline cellulose. Administration of these to neonates is difficult, as P5P has low water-solubility, a phenomenon that is characterized by the yellowish solid residue observed on the dissolution device. The clinical consequence is incomplete administration of the dose, as well as a loss of the nurse's time.

SUMMARY

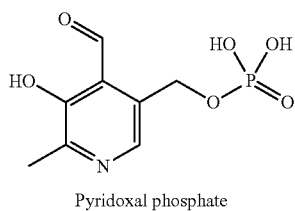 [SMILES: Cc1ncc(COP(=O)(O)O)c(C=O)c1O]

Pyridoxal phosphate

An effervescent galenical formulation has now been developed that dissolves quickly and completely in a suitable volume for administration, allowing a gain of nurse's time, and certainty of administration of the whole dose owing to a change in appearance after dissolution. This formulation also allows addition of flavoring to improve the palatability of the product. More particularly, it was demonstrated that the solubility of P5P in water could be improved considerably by combining P5P with a sodium bicarbonate salt. Thus, when P5P is brought into contact with sodium bicarbonate, there is formation of a P5PNa salt that is more water-soluble than the acid form (P5P-H), while the carbon dioxide formed accelerates the dissolution kinetics by two phenomena:

physical: formation of $CO_2$ bubbles creates effervescence capable of "stirring" the suspension of powder, chemical: release of gaseous $CO_2$ shifts the chemical equilibrium of the reaction toward the right.

$$P5P\text{—}H + NaHCO_3 \leftrightarrow P5PNa + H_2CO_3$$

$$H_2CO_3 \rightarrow H_2O + CO_2$$

This formulation may be supplied in the form of a capsule to be opened.

Thus, according to a first aspect, the invention relates to a pharmaceutical composition comprising:

a mixture M of pyridoxal-5-phosphate (P5P) and of a sodium bicarbonate salt, ($NaHCO_3$), the $P5P/NaHCO_3$ molar ratio being possibly between 0.75 and 1.5, and preferably equal to 1.

at least one pharmaceutically acceptable excipient.

According to an advantageous embodiment, the $P5P/NaHCO_3$ molar ratio is between 0.75 and 1.5; more particularly between 0.78 and 1.5; between 0.80 and 1.5; between 0.85 and 1.5 or between 0.90 and 1.5.

According to another advantageous embodiment, the $P5P/NaHCO_3$ molar ratio is between 0.78 and 1.4; between 0.80 and 1.3; between 0.85 and 1.2; or between 0.90 and 1.1.

According to one embodiment, said mixture M further comprises pyridoxine hydrochloride, the P5P/pyridoxine hydrochloride weight ratio being in particular in the range from 0.5 to 1.5.

The excipient may be selected from a diluent, a sweetener, a flow improver or a mixture thereof. The excipient is notably selected from the excipients that are pharmaceutically acceptable in pediatrics.

As an example of a diluent, we may notably mention isomalt, sucrose, mannitol, sorbitol, lactose, preferably isomalt.

The sweetener may notably be sucralose, sucrose, mannitol.

As an example of a flow improver, we may mention colloidal silica or magnesium stearate, preferably colloidal silica.

According to one embodiment, the excipient is selected from isomalt, sucralose, colloidal silica or a mixture thereof.

According to one embodiment, the mixture M represents 10 to 65 wt % relative to the total weight of the composition.

According to a particular embodiment, the pharmaceutical composition comprises:

10 to 65 wt % of a mixture M of pyridoxal-5-phosphate and sodium bicarbonate,
33 to 85 wt % of isomalt,
0 to 0.3 wt % of sucralose,
0 to 2 wt % of colloidal silica,
said percentages by weight being expressed by weight relative to the total weight of the composition.

According to another particular embodiment, the pharmaceutical composition comprises:

10 to 65 wt % of a mixture M of pyridoxal-5-phosphate, pyridoxine hydrochloride and sodium bicarbonate,
33 to 85 wt % of isomalt,
0 to 0.3 wt % of sucralose,
0 to 2 wt % of colloidal silica,
said percentages by weight being expressed by weight relative to the total weight of the composition.

The pharmaceutical composition according to the invention is notably presented in the form of a dosage form intended for the oral route, in particular in the form of a capsule, to be opened or to be swallowed, the contents of which dissolve in water by effervescence.

According to another aspect, the invention relates to a pharmaceutical composition for use in the treatment of neonatal epilepsy as well as metabolic diseases with a need for derivatives of vitamin B6, in particular for pyridoxal-5-phosphate such as hypophosphatasia, familial hyperphosphatasia including Mabry syndrome linked to deficiency of phosphatidylinositol glycan anchor biosynthetase or type 2 hyperprolinemia linked to deficiency of 1-pyrroline-5-carboxylate dehydrogenase [4].

Definitions

As used herein, the term "pharmaceutically acceptable" refers to excipients that are, on the basis of reasonable medical judgment, suitable for contact with the tissues of human beings and animals without excessive toxicity, irritation, allergic response, or other problematic complications in proportion to a reasonable risk-benefit ratio.

BRIEF DESCRIPTION OF THE DRAWINGS

Figures

DETAILED DESCRIPTION

Examples

TABLE I

| Raw materials and Name of the batches used below | | | | | | |
|---|---|---|---|---|---|---|
| | A | B | C | D | E | Q |
| P5P | + | − | − | − | − | − |
| Sodium bicarbonate | − | + | − | − | − | − |
| Isomalt | − | − | + | − | − | − |
| Sucrose | − | − | − | + | − | − |
| Sorbitol | − | − | − | − | + | − |
| Mannitol | − | − | − | − | − | + |

TABLE II

| Mixtures and Name of the batches used below | | | | | |
|---|---|---|---|---|---|
| | F | G | H | I | J |
| P5P | + | + | + | + | + |
| Sodium bicarbonate | + | + | + | + | + |
| Isomalt | − | + | − | − | − |
| Sucrose | − | − | + | − | − |

TABLE II-continued

| Mixtures and Name of the batches used below | | | | | |
|---|---|---|---|---|---|
| | F | G | H | I | J |
| Sorbitol | − | − | − | + | − |
| Mannitol | − | − | − | − | + |

NB: Batch F: ratio 100 mg of P5P to 34 mg of sodium bicarbonate or 1 equivalent of sodium bicarbonate relative to P5P.

Batches G to J: ratio 50% of premix (P5P+bicarbonate) to 50% of excipients, the percentages being expressed by weight relative to the total weight of the composition.

Example 1: Physicochemical Approach for Selection of the New Galenical Formulation Laser Diffraction Granulometry (European Pharmacopeia (PE), Current Edition, 2.9.31)

Methods:

Analysis of the granulometric distribution was performed in dry mode on a Mastersizer S laser granulometer (Malvern®). The detection range of this instrument in dry mode is from 0.05 µm to 900 µm. This study was performed on 20 g of active principle, at a pressure of 1, 2 and 3 bar. Each test was performed 3 times for each pressure.

Figure 1:
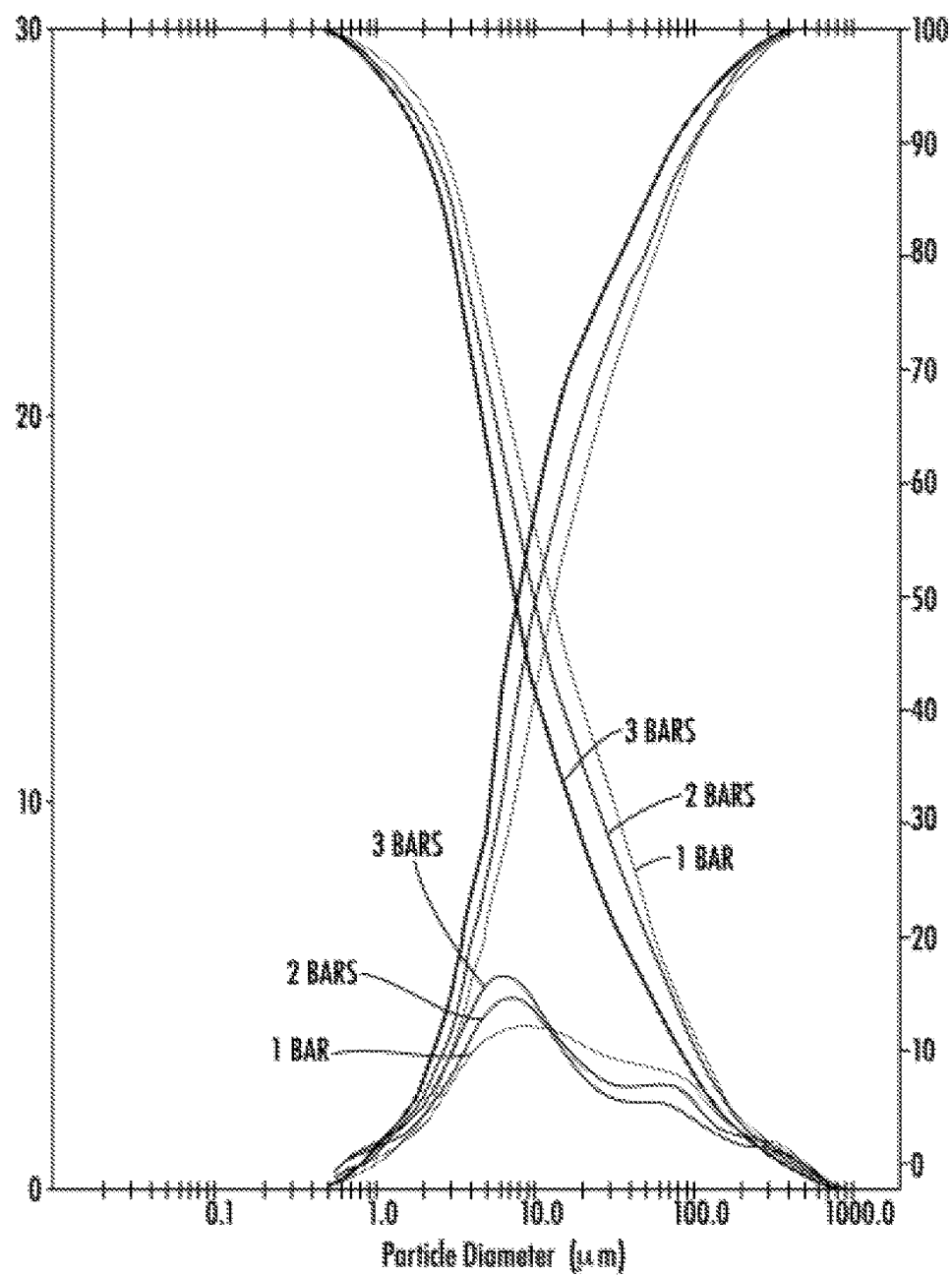
FIG. 1: Laser diffraction granulometry performed on the active principle at 1, 2, 3 bar.

Results:

The particle size of the P5P is below 100 µm (d50=11 µm). However, regardless of the pressure applied, P5P has a first peak with a majority of particles with size between 1 and 10 µm and a second peak with particle size between 50 and 100 µm. This second peak is more pronounced as the pressure increases and notably at 3 bar (FIG. 1).

The powder therefore has two distinct modes with a majority of fine particles below 10 µm.

Example 2: Morphology of the Particles

Methods:

The morphology was determined with an Olympus® SZCTV binocular magnifier (magnification ×40) connected to Videomet® image analysis software. This analysis was performed on the active principle (batch A), sodium bicarbonate (batch B) as well as on the premix (batch F).

Figure 2:
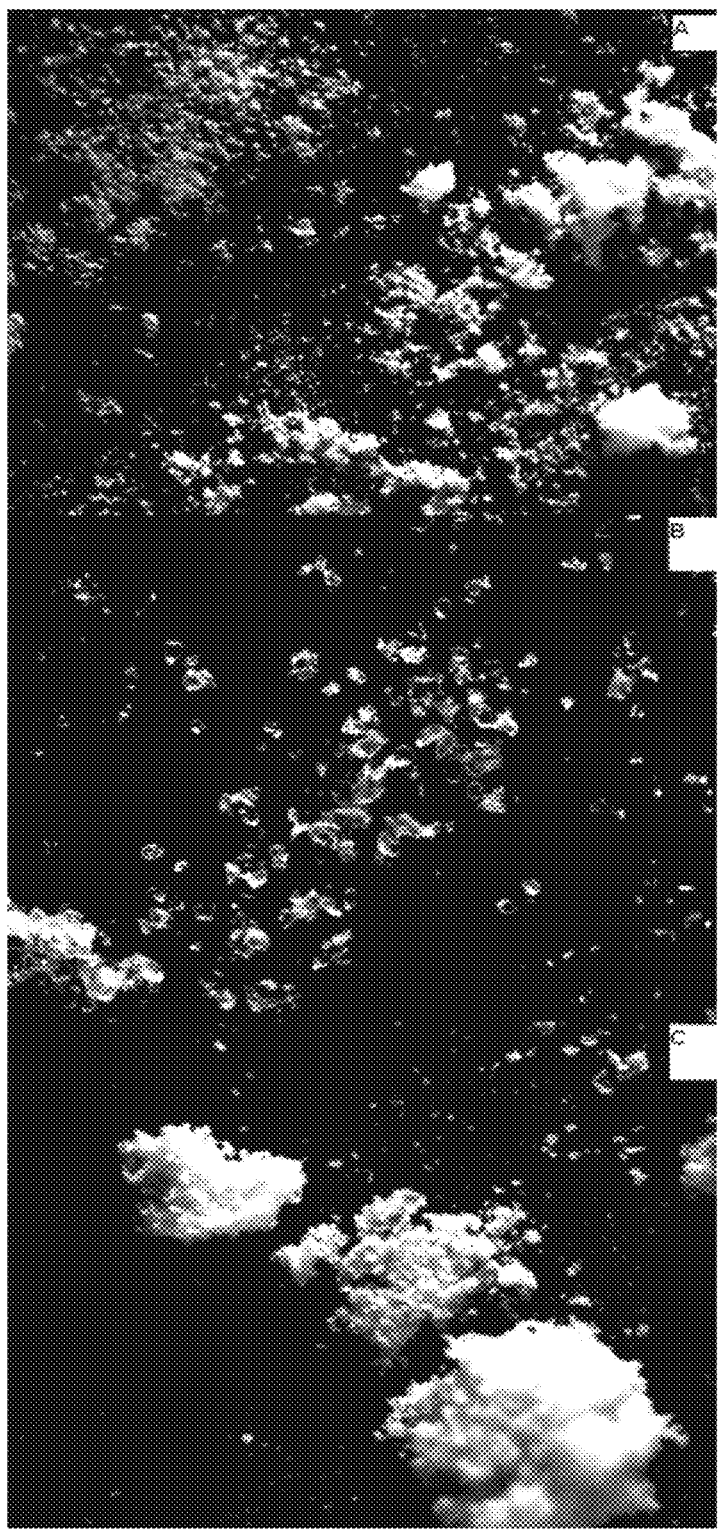
FIG. 2: Appearance and shape of the particles—A: P5P alone, B: sodium bicarbonate and C: P5P/sodium bicarbonate premix.

Results:

Image analysis was performed on P5P, sodium bicarbonate and on the premix (FIG. 2).

Morphological analysis of the P5P shows a flocculent powder of small particle size, with aggregates (Batch A). The sodium bicarbonate shows a crystalline powder of small particle size (Batch B). The premix (100 mg of P5P/34 mg of sodium bicarbonate—Batch C) also has this flocculent appearance, with aggregates as shown previously for batch A, and is made up of two distinct populations. The P5P powder and the premix seem to be very electrostatic. To limit this phenomenon, colloidal silica could be added to the mixtures.

Example 3: Rheology

A. Funnel Flow and Angle of Repose (PE 2.9.16-2.9.36)

Methods:

The tests were performed on an Erweka® flow tester on all of the raw materials and mixtures tested using a standardized funnel. The tests performed on the raw materials were carried out on 100 g of powder, and on 20 g for mixtures (batches A, F, G, H, I, J).

Results:

The excipients (batches B to Q) flow freely as they are excipients that have been functionalized, according to the European Pharmacopeia (Section 1.1 concerning general considerations) to improve their flow, by acting on the particle size, particle shape, and consequently on the relative density of the powders.

TABLE III

| Flow of the different batches | | | | | | | | | | |
|---|---|---|---|---|---|---|---|---|---|---|
| | A | B | C | D | E | Q | F | G | H | I | J |
| Flow (s) | ∞ | 18.1 s | 23.8 s | 22 s | 9.6 s | 27.1 s | ∞ | ∞ | ∞ | ∞ | ∞ |

In contrast, no flow is observed for the active principle (batch A), the premix (batch F) and the mixtures (sucrose for batch G, sorbitol for batch H, isomalt for batch I and mannitol for batch J) despite addition of colloidal silica. However, the electrostatic charges that might really hamper the filling of the hard capsules are no longer observed.

Determination of the angle of repose was performed on the powders alone and on the mixtures, as defined in the European Pharmacopeia. Different mixing times of 5, 10 and 30 minutes were tested on the mixtures (batches of F to J) to determine the influence of the mixing time on the flow (Table IV).

mixed with sodium bicarbonate (batch F), the angle of repose can be measured. There is therefore an improvement in flow due to the excipient.

The excipients tested for direct compression have similar angles of repose, with better flow for batch D (sucrose).

These excipients mixed with P5P and sodium bicarbonate seem to give a slight improvement in the angle of repose of batches G to J starting from 5 minutes. Increasing the mixing time to 30 minutes does not have an effect on the flow of these mixtures.

Consequently, the mixing time can be fixed at 5 minutes.

B. Tapped Density (PE 2.9.34)

Methods:

The tests were performed on a volumenometer (Erweka® GmbH SVM12). The Carr and Hausner indices can be determined by this test. The tests performed on the raw materials were carried out on 100 g of powder, and on 20 g for mixtures (batches A, F, G, H, I, J).

Results:

The tapped density was determined on the raw materials and on the prepared mixtures (Table V).

TABLE IV

| Angles of repose after different mixing times | | | | | | | | | | | |
|---|---|---|---|---|---|---|---|---|---|---|---|
| 5 minutes | A | B | C | D | E | Q | F | G | H | I | J |
| Angle (°) | ∞ | 43.7° | 45° | 40.5° | 43.6° | 38.3° | 50° | 45° | 45° | 42° | 46° |
| Interpretation | — | Passable | Passable | Quite good | Passable | Quite good | Poor | Passable | Passable | Passable | Poor |
| 10 minutes | A | B | C | D | E | Q | F | G | H | I | J |
| Angle (°) | N.R. | N.R. | N.R. | N.R. | N.R. | N.R. | 42° | 45° | 45° | 42° | 46° |
| Interpretation | N.R. | N.R. | N.R. | N.R. | N.R. | N.R. | Passable | Passable | Passable | Passable | Poor |
| 30 minutes | A | B | C | D | E | Q | F | G | H | I | J |
| Angle (°) | N.R. | N.R. | N.R. | N.R. | N.R. | N.R. | 42° | 43° | 45° | 42° | 46° |
| Interpretation | N.R. | N.R. | N.R. | N.R. | N.R. | N.R. | Passable | Passable | Passable | Passable | Poor |

N.R.: Not Done

The angle of repose of P5P alone cannot be interpreted, because the powder does not flow. Nevertheless, when it is

TABLE V

| Principal characteristics after tamping | | | | | | | | | | |
|---|---|---|---|---|---|---|---|---|---|---|
| A | B | C | D | E | Q | F | G | H | I | J |
| Compactibility (mL) | | | | | | | | | | |
| NR | 5 | 8 | 3 | 9 | 0 | 5 | 5 | 2 | 5 | 2 |
| Hausner ratio (<1.20) | | | | | | | | | | |
| so so | 1.18 Good | 1.13 Good | 1.10 Excellent | 1.10 Excellent | 1.02 Excellent | 1.43 Poor | 1.33 Passable | 1.21 Quite good | 1.29 Passable | 1.25 Quite good |

TABLE V-continued

| | | | | Principal characteristics after tamping | | | | | |
|---|---|---|---|---|---|---|---|---|---|
| A | B | C | D | E | Q | F | G | H | I | J |
| | | | | Carr index (<20%) | | | | | |
| so | 15 | 11.25 | 8.70 | 9.05 | 7.48 | 30 | 25 | 17.5 | 22.2 | 26 |
| so | Good | Good | Excellent | Excellent | Excellent | Poor | Passable | Good | Passable | Poor |

Regarding compactibility (V10-V500), regardless of the powder, and regardless of the mixture, all the batches show a difference of less than 20 mL. These mixtures show little settlement and would therefore be favorable for putting in hard capsules.

For the Carr index (Ic) and the Hausner ratio (Ih), all the excipients display very good flow with Ic and Ih below 20% and 1.20, respectively. Moreover, in a mixture with P5P and bicarbonate (Batch G to J), the indices are improved compared to the premix (batch F).

Furthermore, all the excipients tested seem very similar to one another.

Regardless of the method for quantifying the flow, the excipients tested make it possible to improve the flow of the various mixtures. This is most probably due to the fact that they are excipients that have been functionalized to improve their flow.

Example 4: Dissolution Tests According to Nursing Practice of 10 mg of P5P in 2 mL of Sterile Water for Irrigation of the New Galenical Formulation (Formulation A) and of the Formulation of the Prior Art (Formulation B)

Formulation A was prepared as follows:

10 mg of P5P, 4.5 mg of sodium bicarbonate, and 0.2 mg of colloidal silica were weighed separately.

The P5P and then the colloidal silica were put in a mortar of a suitable size, and mixed. Then the sodium bicarbonate was added, and the whole was mixed.

About 150 mg of isomalt, as diluent, required for manufacture of the hard capsules (size No. 4) was then added.

The mixture of powder obtained was then packaged in the hard capsules.

Formulation B was prepared as follows:

10 mg of P5P was weighed, and the required amount of diluent for preparing the No. 4 hard capsules, in this case microcrystalline cellulose, was then added. The whole was mixed in a mortar and The mixture of powders obtained was then packaged in the hard capsules.

To simulate the preparation of the treatment at the patient's bedside, repeated measurements were taken with a stopwatch of the dissolution of 1 hard capsule of size No. 4 containing the formulation according to the invention (Formulation A) relative to a hard capsule of size No. 4 containing formulation B.

The stopwatch was stopped at 180 seconds if dilution was not complete. The experiment was carried out on 5 hard capsules of each formulation (10 mg of P5P in 2 mL of water).

Figure 3:
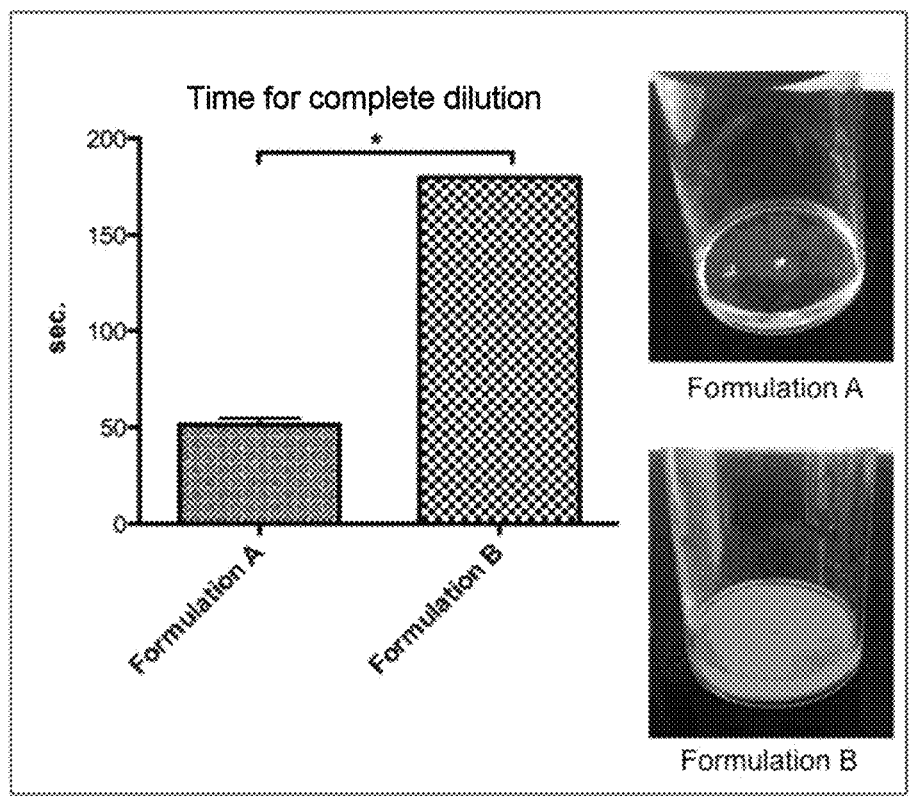
FIG. 3: Diagram showing the average dilution time of the hard capsules of P5P according to the formulation of the invention (<1 min) (formulation A) and according to the formulation of the prior art (formulation B).

The results obtained are presented in FIG. 3. It can be seen that the average dilution time is less than 1 minute for formulation A and greater than 180 seconds for formulation B. For the latter, after 180 seconds, we observe incomplete dissolution of the P5P and of the microcrystalline cellulose, which remain in suspension.

Example 5: Study of Stability Over Time of the Content of Pyridoxal-5-Phosphate in Effervescent Formulations Containing Pyridoxal-5-Phosphate (P5P)

Two batches of capsules containing an effervescent formulation comprising P5P, sodium bicarbonate, colloidal silica and isomalt in the same proportions as in formulation A, but with 25 mg and 50 mg of P5P respectively, were prepared according to example 4. These two batches, produced separately, were stored in standard temperature conditions.

P5P assay was performed (HPLC UV 205 nm) on 10 capsules at 11 days, 48 days and 312 days after manufacture for the capsules after 25 mg and at 15 days, 52 days and 316 days after manufacture of the 50 mg capsules (FIG. 4).

Figure 4A:
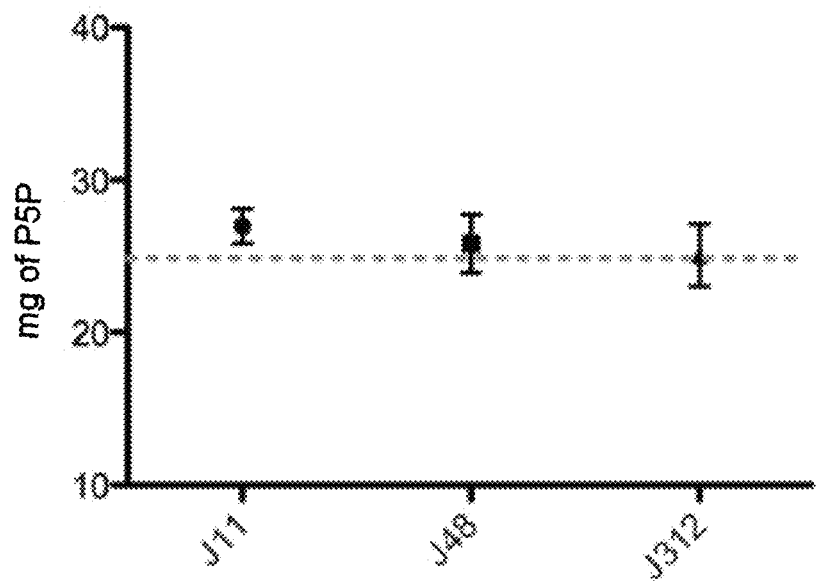
FIG. 4: Diagram showing the mean values and standard deviations relating to the capsules containing 25 mg of P5P (FIG. 4A) and 50 mg of P5P (FIG. 4B), respectively, at different analysis times after manufacture.

The mean values and standard deviations were, for 10 25 mg capsules, 26.9±1.1 mg at 11 days, 25.8±1.9 mg at 48 days and 25.1±2 mg at 312 days after manufacture (FIG. 4A).

Figure 4B:
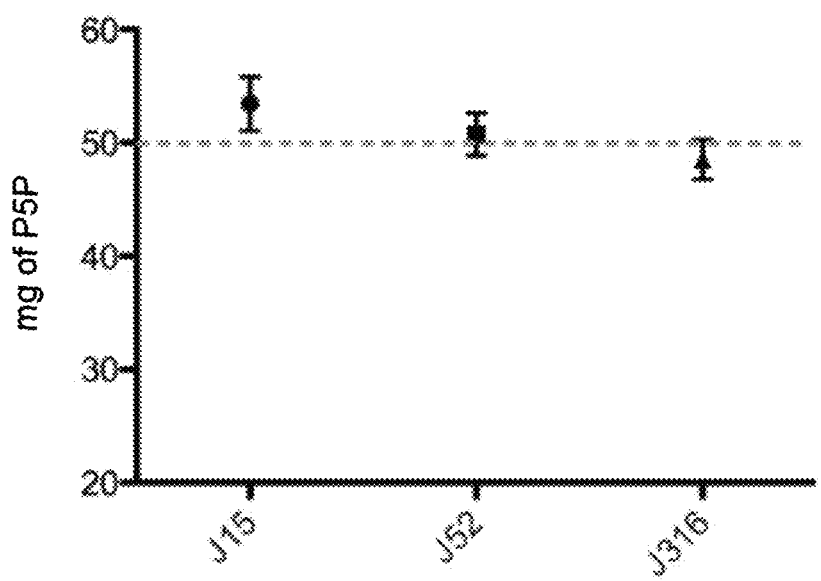

The mean values and standard deviations were, for 10 50 mg capsules, 53.4±2.4 mg at 15 days, 50.8±1.9 mg at 52 days and 48.6±1.8 mg at 316 days after manufacture (FIG. 4B).

Example 6: Preparation of a Formulation Comprising P5P and Pyridoxine Hydrochloride This formulation is prepared as follows:

10 mg of P5P, 10 mg of pyridoxine hydrochloride, 4.5 mg of sodium bicarbonate, and 0.2 mg of colloidal silica are weighed separately.

The P5P and the pyridoxine hydrochloride, and then the colloidal silica, are put in a mortar of a suitable size, and mixed. Then the sodium bicarbonate is added, and the whole is mixed.

About 150 mg of isomalt, as diluent, required for manufacture of the hard capsules (size No. 4) is then added.

The mixture of powder obtained is then packaged in the hard capsules.

It should be noted that the respective amounts of P5P, of pyridoxine hydrochloride and of the excipients may be increased or decreased according to the desired additions, the amount of sodium bicarbonate then being adapted to that of P5P, according to the present invention.

REFERENCES

1. Ronen G M, Penney S, Andrews W. The epidemiology of clinical neonatal seizures in Newfoundland: a population-based study. J Pediatr 1999; 134: 71-5.2.

2. Saliba R M, Annegers J F, Waller D K, Tyson J E, Mizrahi E M. Incidence of neonatal seizures in Harris County, Tex., 1992-1994. Am J Epidemiol 1999; 150: 763-9.
3. Booth & Evans. Anticonvulsants for neonates with seizures. Cochrane Database Syst Rev 2004; 4: CD004218.
4. Ingrid Tein Vitamin and Cofactor Responsive Encephalopathies and Seizures ICNA 2015; 15: 105.

The invention claimed is:

1. A method for the treatment of neonatal epilepsy in a patient in need thereof, comprising the step of administering a pharmaceutical composition comprising:
   10 to 65 wt % of a mixture M of pyridoxal-5-phosphate (P5P) and sodium bicarbonate ($NaHCO_3$), the P5P/$NaHCO_3$ molar ratio being between 0.75 and 1.5,
   33 to 85 wt % of isomalt,
   sucralose being present, and in an amount up to 0.3 wt %,
   colloidal silica being present, and in an amount up to 2 wt %,
said percentages by weight being expressed by weight relative to the total weight of the composition.

2. The method of claim 1, wherein the P5P/$NaHCO_3$ molar ratio is equal to 1.

3. The method of claim 1, wherein the the mixture M further comprises pyridoxine hydrochloride.

4. The method of claim 1, wherein the composition is in the form of a dosage form intended for the oral route.

5. The method of claim 1, wherein the composition is in the form of a capsule, to be opened or to be swallowed.

* * * * *